(12) United States Patent
Giersch

(10) Patent No.: US 6,410,504 B1
(45) Date of Patent: Jun. 25, 2002

(54) NITRILES AND ALDEHYDES DERIVED FROM 3-ISOPROPENYL-1,2-DIMETHYL-1-CYCLOPENTANOL AND THEIR USE IN PERFUMERY

(75) Inventor: Wolfgang Giersch, Bernex (CH)

(73) Assignee: Firmenich, SA, Geneva (CH)

( * ) Notice: Subject to any disclaimer, the term of this patent is extended or adjusted under 35 U.S.C. 154(b) by 0 days.

(21) Appl. No.: 09/722,439

(22) Filed: Nov. 28, 2000

Related U.S. Application Data

(62) Division of application No. 09/185,535, filed on Nov. 4, 1998, now Pat. No. 6,180,814.

(30) Foreign Application Priority Data

Nov. 11, 1997 (CH) .............................................. 2592/97

(51) Int. Cl.[7] .............................. A61K 7/46; A61K 7/32; A61K 7/06; A61K 7/075; A61K 7/50
(52) U.S. Cl. .......................... 512/1; 424/65; 424/70.1; 424/401; 510/119; 510/130; 510/135; 510/102; 510/158; 510/159; 510/276; 512/6; 514/530; 514/844
(58) Field of Search .................. 424/401, 65, 70.1; 512/1, 6; 514/530, 844; 510/119, 130, 135, 158, 159, 102, 276

(56) References Cited

U.S. PATENT DOCUMENTS 4,168,281 A 9/1979 Gray et al. .................. 260/598

FOREIGN PATENT DOCUMENTS

| DE | 24 47 170 | 4/1976 |
|---|---|---|
| FR | 2 372 784 | 6/1978 |
| GB | 1 550 004 | 8/1979 |

OTHER PUBLICATIONS

Chalk, "Hydroformulation of Terpenes and Related Molecules", *Chem. Ind.* (Dekker), 33 (*Catal. Org. React.*), 43–63 (1998).

Strickler et al., "78. Zur Kenntnis der ätherischen Öle. Die thermische Cyclisation des (–)–(R)–Linalools.", *Helvetica Chimica Acta*, vol. 50, 759–797 (1967).

*Primary Examiner*—Jose' G. Dees
*Assistant Examiner*—Marina Lamm
(74) *Attorney, Agent, or Firm*—Winston & Strawn

(57) ABSTRACT

The compounds of formula

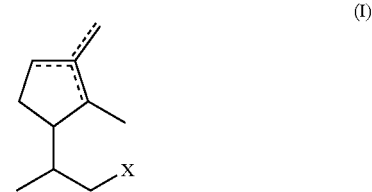

(I)

in which X is a C≡N group or a C(H)=O group and the $C_5$-ring is either saturated or carries a double bond in one of the positions indicated by the dotted lines, or any mixture of two or more compounds of formula (I), are described.

The compounds and mixtures were found to be useful as perfuming ingredients, with the compounds of the above formula in which X is a C≡N group and the $C_5$-ring has a double bond in one of the positions indicated by the dotted lines, being particularly stable in aggressive media. The odor note of these compounds is quite close to that of citral, i.e. of the fresh-citrus type with green and lime connotations.

28 Claims, No Drawings

NITRILES AND ALDEHYDES DERIVED FROM 3-ISOPROPENYL-1,2-DIMETHYL-1-CYCLOPENTANOL AND THEIR USE IN PERFUMERY

This is a divisional of application Ser. No. 09/185,535, filed Nov. 4, 1998 now U.S. Pat. No. 6,180,814.

BRIEF SUMMARY OF THE INVENTION

The present invention relates to the field of perfumery. It concerns, more particularly, the compounds of formula

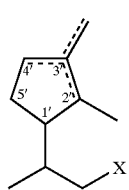

(I)

wherein X represents a C≡N group or a C(H)=O group and the $C_5$-ring is either saturated or carries a double bond in one of the positions indicated by the dotted lines, or any mixture of two or more compounds of formula (I), and their use in perfumery.

BACKGROUND OF THE INVENTION

The compounds as defined by the above formula (I) are novel compounds, and their use in perfumery has never been described or suggested. They carry an aldehyde function or a nitrile function and all have a characteristic, green-lemon type odor which is of considerable value in perfumery.

One embodiment of the invention is drawn to the compounds of the above formula (I) in which X is a C≡N group, i.e. belonging to the nitrile chemical family, which are particularly appropriate for use in aggressive media. A further embodiment are the corresponding aldehydes of similar chemical structure which show the same odor type as the said nitriles.

It should be mentioned that a large number of compounds belonging to the nitrile chemical family are known in the perfume industry. In the context of the present invention, one can cite the nitrites specified hereinafter, which are currently used in perfumery, in particular in functional perfumery.

Geranyl nitrile (3,7-dimethyl-2,6-octadienenitrile) possesses a strong green, chemical odor resembling that of citral (Z-3,7-dimethyl-2,6-octadienal), the latter being itself a compound of widespread use in perfumery applications and of natural occurrence.

Citronellyl nitrile (3,7-dimethyl-6-octenenitrile) shows an olfactive note reminiscent of the odor of lemon, with an undernote characteristic of the nitrites. The citrus note is likewise quite pronounced in Ozonil® (mixture of 2-tridecenenitrile and 3-tridecenenitrile; origin: Haarmann & Reimer, Germany), but there are also present notes of the mandarine-fruity, peach type, which are associated with a floral undernote.

Finally, citronitrile (3-methyl-5-phenyl-2-pentenenitrile) shows an odor of the same type as the compounds mentioned beforehand, namely of the fruity-citrus type.

Detergents, deodorants or antiperspirants and soaps are examples of products which are aggressive media, in which citral, for example, which can be considered as the typical compound representing the citrus-type odor, with its powerful citrus-green note, is unstable, preventing it from being used in functional perfumery, and this in spite of its odor which is very prized by perfumers.

Now, in spite of showing olfactive similarities with citral, the known nitrites described above do not possess its olfactive quality. Their odor notes are less characteristic of lemon, less fresh-citrus, and a fatty-metallic connotation is found in all these nitrites. For these reasons, the search for nitrites stable in aggressive media and possessing an odor close to the citrus-green note of the odor of citral continues to be a task of actuality.

DETAILED DESCRIPTION OF THE INVENTION

The present invention provides novel compounds having this desired odor and brings an original solution to exactly this problem.

We have in fact found that, in particular, the compounds of formula

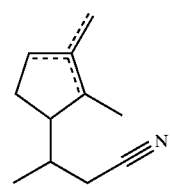

(I')

having a double bond in one of the positions indicated by the dotted lines, or any mixture of two or more of these compounds, not only possess an excellent stability in aggressive media, but also an odor which is very similar to that of citral.

Thus, the odor of the compounds of formula (I'), or of the mixtures of these, possess the same fresh-citrus connotation as citral, quite unexpected for a nitrile. There is also found a green connotation reminiscent of lime, and the compounds of the invention do not have the fatty-metallic connotation generally found in nitrites of current use in perfumery (see above for current examples). Generally speaking, the odor of the compounds of the invention is very fresh and clean.

According to the invention, it is preferred to use as perfuming ingredient, a mixture of the compounds of formula (I') containing at least about 30% by weight of the compound of formula

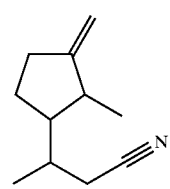

(I'a)

Even more preferred are the above-mentioned mixtures containing, besides the compound (I'a) in the specified amount, about 60% by weight of the compound of formula

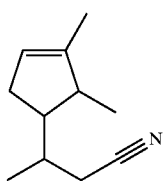

(I'b)

having an endocyclic double bond in position 3' of the ring.

According to an even more preferred embodiment of the invention, there will be used a compound of formula (I'a) in its pure state, representing at its best the fresh-citrus, green-lime note of citral.

It has however been found that the above-mentioned olfactive characteristics are also present in the mixtures as specified above, satisfactory for the perfumers' criteria and thus the said mixtures are also useful as perfuming ingredients. The advantage of the use of these mixtures, compared to that of the compounds contained therein in their pure state is an economical one, given the fact that these mixtures can be directly obtained from the synthesis described below, without requiring the use of particular separation techniques.

The nitriles of the present invention are accessible by a multi-stage synthesis which makes use of 3-isopropenyl-1,2-dimethyl-1-cyclopentanol, or one of its optically active isomers, as starting product. This cyclic alcohol is a commercially available compound, formed in the pyrolysis reaction of (−)-R-linalool and leading to a mixture of four diastereomers (see H. Strickler, G. Ohioff and E.sz.Kovàts, HelV. Chim. Acta 1967 50, 759).

The synthesis we have developed for the nitriles of formula (I) is outlined in the scheme below:

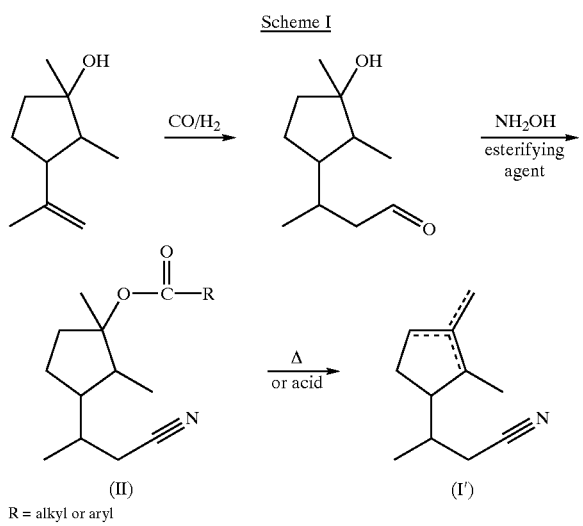

Scheme I

R = alkyl or aryl

The first step of this synthesis comprises the hydroformylation of the cyclic starting alcohol, to form the corresponding aldehyde. The hydroformylation reaction being known to a person skilled in the art, the latter can choose the appropriate reaction conditions, for example the catalyst, solvent or pressure giving good results, without a more detailed description being necessary here.

The thus-obtained aldehyde is then transformed into the corresponding nitrile, for example by using hydroxylamine or a salt thereof, in the presence of a base. In the following step, the compound obtained is esterified with a current esterifying agent, for example acetic anhydride. It was found to be advantageous not to isolate the above-mentioned intermediate nitrile from the reaction mixture, but to directly esterify said nitrile in the same medium in which it had been prepared.

The last step of the process is the elimination reaction of the thus-obtained ester (II), preferably of 3-(2'-cyano-1-methylethyl)-1,2-dimethyl-1-cyclopentyl acetate, leading to the desired final product, namely the unsaturated nitriles of formulae (I'a) and (I'b). The elimination reaction can be carried out under various conditions which are known to a person skilled in the art. In this context, one should mention the use of an acid, for example p-toluenesulfonic acid, to carry out the elimination reaction.

The best results were however obtained by a thermal treatment, i.e. a pyrolysis of the nitrile ester, resulting in a crude product containing an olfactively satisfactory amount of the most desired nitrile (I'a), whereas the elimination reaction with an acid often results in the preferential formation of nitrites having double bonds in endocyclic position, i.e. those of above formula (I'b) and of formula (I'c) below:

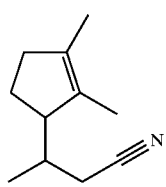

(I'c)

which are less appreciated from an olfactive point of view.

We have found that products containing about 30% by weight of the nitrile of formula (I'a) could be obtained when the pyrolysis reaction was carried out at a temperature range from about 400 to 550° C., preferably from about 430 to 500° C., and under a pressure from about 10 to $50 \times 10^2$ Pa. These mixtures contain, besides the compound (I'a), the nitrites of formulae (I'b) and (I'c), with their respective amounts varying according to the conditions employed.

These mixtures can be used as such as perfuming ingredients, since they have all the olfactive characteristics of the nitrile (I'a), i.e. the typical fresh-citrus, green-lemon note, the overall impression being practically as good as that of this nitrile in its pure form.

It is of course possible to use mixtures of the above-described type containing amounts of the nitrile (I'a) different from the quantity mentioned above (30% by weight), as long as said nitrile is present in an effective amount, i.e. in an amount sufficient to bring out the olfactive character of the mentioned nitrile. We have however found that mixtures containing 30% or more of this nitrile were preferred according to the invention.

Of course, since the pyrolysis reaction of (−)-(R)-linalol results in a mixture of four diastereomers which each can be isolated by current techniques, each of these diastereomers can then be used separately to prepare the desired nitrites, the stereochemistry of the latter being thus determined by that of the starting diastereomer employed, which remains unchanged throughout the synthesis outlined above. This will become more obvious from the study of the examples further on. According to their stereochemistry, the odor of the compounds of formula (I'a) having a defined stereochemistry can be different from that of a mixture of diastereomers.

It was found that the best olfactive quality is obtained when the cyclopentanol used as starting product has the configuration (1R,2S,3S), resulting in a mixture which is composed of the nitriles of formula (I'a) having the configuration (1'R,2'S,3S) and (1'R,2'S,3R) and the nitrites of formula (I'b) having the configuration (1'R,2'S,3R) and (1'R,2'S,3S). These mixtures, and in particular the stereoisomers of formula (I'a) as described above, are preferred according to the invention.

A nitrile mixture of almost similar quality was obtained with the cyclopentanol of configuration (1R,2R,3R), resulting in a final mixture of the nitrites of formula (I'a) of configuration (1'S,2'R) and of formula (I'b) of configuration (1'S,2'R).

The olfactive quality of the mixture obtained from the cyclopentanol of configuration (1R,2S,3R), i.e. of the mixture of nitrites of formula (I'a) having the configuration (1'S,2'S) and the nitrites of formula (I'b) having the configuration (1'S,2'S), is inferior to the quality of the nitrites obtained above. Here, the lemon note is weaker, and fatty and powdery connotations are perceived, the floral-citrus note being still clearly present, however.

The compound 3-(2,3-dimethyl-1-cyclopentyl) butanenitrile of formula (I'd) (see Scheme II below), having a saturated $C_5$-ring, has also been found to possess the typical green-lemon note in its odor, with a slight nitrile connotation.

A further embodiment of the invention are the aldehydes of the formula (I") represented below having a double bond in one of the positions indicated by the dotted lines or any mixture of two or more of these compounds. The following Scheme (II) outlines the synthesis for these aldehydes, as well as the synthesis for the corresponding ring-saturated aldehydes of formula (I"a).

Scheme II

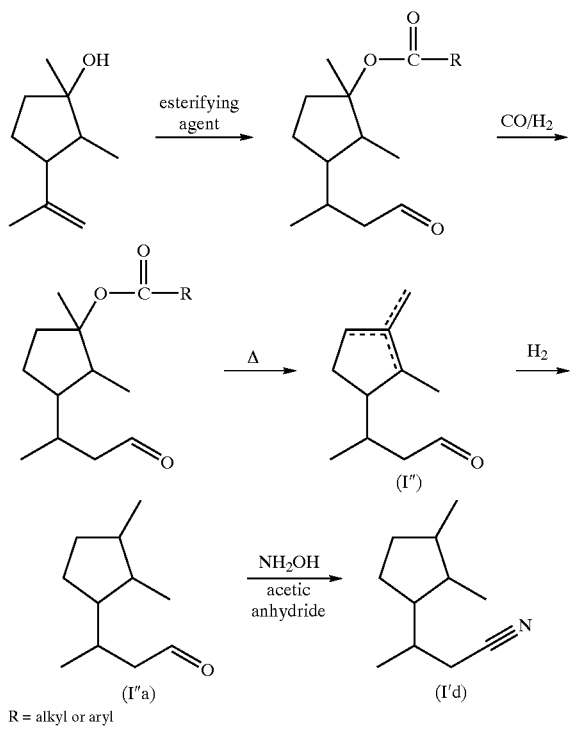

R = alkyl or aryl

The ring unsaturated aldehydes of formula (I") are useful in perfumery due to their fresh-citrus and green-lemon type note with a typical aldehyde connotation. The odor type is close to that of 3,5,5-trimethylhexanal (isononylaldehyde), which is a compound of widespread use in perfumery, capable of imparting notes of the green type to a composition.

The corresponding ring saturated aldehyde (I"a) has a green-citrus type odor, with an earthy and slightly metallic connotation and a lemongrass type undernote.

The nitriles of the present invention were found to be completely stable in a lot of typically aggressive media for perfumes. In this context, there can be cited detergents containing bleaching agents and activators such as, for example, tetraacetylethylenediamine (TAED), hypohalites, in particular hypochlorite, peroxygenated bleaching agents such as, for example, perborates, etc. One can also cite body deodorants and antiperspirants containing for example aluminum salts.

Generally speaking, the nitrites of the present invention are preferably employed in applications like soaps, shampoos, body deodorants and antiperspirants, solid or liquid detergents for the treatment of textiles, fabric softeners, or yet detergent compositions or all-purpose cleaners for the cleaning of dishes or various surfaces, whether they are intended for household or industrial use.

Of course, the use of the nitrites of the invention is not limited to the above-mentioned products, they lend themselves to all other current uses in perfumery, namely the perfuming of soaps and shower gels, hygiene or hair-care products, as well as of body deodorants, air fresheners or yet cosmetic preparations, and even for the use in fine perfumery, namely in perfumes and colognes.

The aldehydes of the present invention can also be used in all the applications cited above.

In all cited applications, the compounds of the invention can be used alone or in admixture with other perfuming ingredients, solvents or adjuvants of current use in the art. The nature and the variety of these coingredients do not require a more detailed description here, which, moreover, would not be exhaustive, and the person skilled in the art will be able to choose the latter through its general knowledge and as a function of the nature of the product to be perfumed and of the desired olfactive effect.

These perfuming ingredients belong to chemical classes as varied as alcohols, aldehydes, ketones, esters, ethers, acetates, nitrites, terpene hydrocarbons, sulfur- and nitrogen-containing heterocyclic compounds, as well as essential oils of natural or synthetic origin. A large number of these ingredients is moreover listed in reference textbooks such as the book of S. Arctander, Perfume and Flavor Chemicals, 1969, Montclair, N.J., USA, or its more recent versions, or in other works of similar nature.

The proportions in which the compounds according to the invention can be incorporated in the various products mentioned beforehand vary within a large range of values. These values depend on the nature of the article or product that one desires to perfume and the odor effect searched for, as well as on the nature of the coingredients in a given composition when the compounds of the invention are used in admixture with perfuming coingredients, solvents or adjuvants of current use in the art.

As an example, there can be cited typical concentrations of the order of 0.1 to 10%, or even more, by weight of these compounds relative to the weight of the perfuming composition in which they are incorporated. Far lower concentrations than those mentioned above can be used when the compounds are directly applied for perfuming the various consumer products cited beforehand.

The invention will now be described in greater detail by way of the following examples in which the abbreviations

EMBODIMENTS OF THE INVENTION

EXAMPLE 1

Preparation of the Unsaturated Nitriles of the Invention

A. Hydroformylation of 3-Isopropenyl-1,2-dimethyl-1-cyclopentanol (General Procedure for all Isomers)

An autoclave was charged with 900 g (5.4 mole) of 3-isopropenyl-1,2-dimethyl-1-cyclopentanol, 63 g (0.24 mole; origin: Glidco) of triphenylphosphine and 0.6 g (0.65 mmole) of [(C$_6$H$_5$)$_3$P]$_3$Rh(CO)H. The autoclave was closed, pressurized with a CO/H$_2$ mixture (1:1) to 14×10$^5$ Pa and heated to 110°. After 5 days, the reaction was stopped to obtain 920 g (60% conversion) of crude product. The thus-obtained mixture was distilled at 102–105° (6×10$^1$ Pa), after which 400 g (2.17 mole) of 3-(3'-hydroxy-2',3'-dimethyl-1'-cyclopentyl)butanal were obtained.

Spectral data of the isomer of configuration (1'R,2'S,3'R), prepared from (1R,2S,3S)-3-isopropenyl-1,2-dimethyl-1-cyclopentanol:

$^1$H-NMR: 0.88/0.90 (two d, J=7, 3H); 0.93 (d, J=7, 3H); 0.97(d, J=6,5, 3H); 1.33 (s, 3H); 9.78(broad s, 1H) δ ppm; $^{13}$C-NMR: (first isomer): 8.43 ; 18.59; 25.33; 29.86; 29.93; 37.7; 45.03; 46.86; 49.54; 80.04; 202.83 δ ppm; (second isomer): 8.75; 19.48; 25.59; 29.86; 30.27; 37.73; 45.03; 47.25; 49.94; 80.10; 203.22 δ ppm; MS: (first isomer): 184(M+,1), 169(2), 166(2), 151(6), 123(11), 108(38)95 (22), 81(18), 71(98), 43(100); (second isomer): 184(M+,0), 169(1), 166(4), 151(5), 123(13), 108(33), 95(32), 81(36), 71(97), 43(100).

B. Synthesis of 3-(2'-Cyano-1'-methylethyl)-1,2-dimethyl-1-cyclopentyl Acetate (General Procedure for all Isomers)

The product mixture obtained in A. above (202 g, 1.9 mole), NH$_2$OH-HCl (98 g, 1.4 mole) and KOH (91 g, 1.6 mole) in toluene (1.5 l) were refluxed for 150 minutes under stirring. The mixture was then cooled to room temperature and washed with water (400 ml), then with brine (400 ml). The thus-obtained solution was then heated to reflux, and 500 ml of toluene were distilled off. There were then added 800 g (7.84 mole) of acetic anhydride, with the temperature of the mixture being maintained. When the reaction was finished, the solvent was removed by distillation and the residue was distilled, to obtain the desired product which was composed of two diastereomers in a yield of 84% (206 g).

Boiling point: 100° (5×10$^1$ Pa).

Spectral data of the isomer of configuration (1R,2S,3R), prepared from (1'R,2'S,3'R)-3-(3'-hydroxy-2',3'-dimethyl-1'-cyclopentyl)butanal:

$^1$H-NMR: 0.77/0.78 (two d, J=8, 3H); 1.1/1.12 (two d, J=6, 3H); 1.52 (s, 3H); 2.01 (s, 3H) δ ppm; $^{13}$C-NMR: (first isomer): 8.93; 18.6; 23.51; 23.86; 25.54; 32.52; 35.2; 43.49; 45.11; 88.68; 170.17 δ ppm; (second isomer): 8.74; 18.18; 23.34; 23.86; 25.47; 32.52; 35.11; 43.22; 44.99; 88.61; 170.17 δ ppm; MS: (first isomer): 223 (M$^+$,0), 183(3), 165(21), 152(12), 123(18), 110(23)95(17), 71(20), 43(100). (second isomer): 223(M$^+$,0), 183(2), 165(26), 152(6), 123 (20), 110(11)95(20), 71(25), 43(100).

C. Pyrolysis of 3-(2'-Cyano-1'-methylethyl)-1,2-dimethyl-1-cyclopentyl Acetate (General Procedure for all Isomers)

The product obtained in B. above was pyrolyzed at 450° and 2×10$^3$ Pa in a column having a length of 2 m and a diameter of 30 mm. There was thus obtained a mixture containing about 30% of compound (I'a), about 63% of compound (I'b) and traces of compound (I'c). The mixture obtained could be used as such as perfuming ingredient. It is however possible to separate compound (I'a) from compound (I'b); it is likewise possible to separate the respective isomers of each of the compounds (I'a) and (I'b), for example by gas chromatography.

Spectra of the compounds obtained from (1R,2S,3R)-3-(2'-cyano-1'-methylethyl)-1,2-dimethyl-1-cyclopentyl acetate:

(1'R,2'S,3S)-3-(2'-methyl-3'-methylene-1'-cyclopentyl) butanenitrile (15%)

$^1$H-NMR: 0.90(d, J=8, 3H); 1.12(d, J=6, 3H); 4.8 and 4.6 (two broad s, 2H) δ ppm; MS: 163(M$^+$,2): 148(4), 123(7), 107(5), 95(100), 79(13), 67(24), 41(11); Odor; described above.

(1'R,2'S,3R)-3-(2'-methyl-3'-methylene-1'-cyclopentyl) butanenitrile (15%)

$^1$H-NMR: 0.90(d, J=8, 3H); 1.14(d, J=6, 3H); 4.79 and 4.86 (two broad s, 2H) δ ppm; MS: 163(M$^+$,2): 148(3), 123(4), 107(5), 95(100), 79(11), 67(21), 41(19); Odor: described above.

1'R,2'S,3R)-3-(2'-3'-dimethyl-3-cyclopentene-1'-yl )butanenitrile (29%)

$^1$H-NMR: 0.83(d, J=8, 3H); 1.09(d, J=6, 3H); 1.69 (splitted d, 3H); 5.66 (broad s, 1H) δ ppm; MS: 163(M$^+$,6): 148(6), 120(8), 107(18), 95(100), 79(12), 67(16), 41(15).

(1('R,2'S,3S)-3-(2'-3'-dimethyl-3-cyclopentene-1-yl) butanenitrile (33%)

$^1$H-NMR: 0.84(d, J=8, 3H); 1.14(d, J=6, 3H); 1.70 (splitted d, 3H); 5.24 (broad s, 1H) δ ppm; MS: 163(M$^+$,7): 148(6), 123(3), 107(17), 95(100), 79(11), 67(16), 41(15).

Spectra of the compound mixture obtained from (1R,2S,3S)-3-(2'-cyano-1'-methylethyl)-1,2-dimethyl-1-cyclopentyl acetate [mixture of (1'S,2'S)-3-(2',3'-dimethyl-3'-cyclopenten-1'-yl)butanenitrile and (1'S,2'S)-(2'-methyl-3'-methylene-1'-cyclopentyl)butanenitrile]:

$^1$H-NMR (mixture): 0.92–1.18(several d, 6H); 1.63 (br. s, 3H); 4.78–4.86 (two spl. s, C═CH$_2$), 5.22 (br. s, C═CH); MS: 163(M$^+$,12): 148(10), 120(17), 110(15), 107(27), 95(100), 79(21), 67(27), 41(31) (not attributed); MS: 163. M$^+$,2): 148(3), 120(3), 95(100), 79(11), 67(20), 40(40) (not attributed); MS: 163(M$^+$,2): 148(3), 120(6), 95(100), 79(13), 67(23), 41(23), (not attributed).

The mixture was composed of 4 isomers, 2 of which can be separated by gas chromatography. The configuration of the nitriles present in the mixture was attributed from the configuration of the starting cyclopentanol.

Spectra of the compound mixture obtained from (1R,2R,3S)-3-(2'-cyano-1'-methylethyl)-1,2-dimethyl-1-cyclopentyl acetate [mixture of (1'S,2'R)-3-(2',3'-dimethyl-3'-cyclopenten-1'-yl)butanenitrile and (1'S,2'R)-(2'-methyl-3'-methylene-1'-cyclopentyl)butanenitrile]:

$^1$H-NMR (mixture): 0.8–0.85 (several d, 3H); 1.1–1.18 (several d, 3H); 1.62 and 1.7 (two br. s, 3H); 4.79 and 4.85 (two spi. s, C═CH$_2$); 5.25 br. s (C═CH); MS: 163(M$^+$,7): 95(100), 77(7), 67(16), 41(12) (not attributed); MS: 163(M$^+$, 7): 148(7), 120(8), 107(18), 95(100), 79(13), 67(18), 41(20) (not attributed); MS: 163(M$^+$,8): 95(100), 77(7) (not attributed).

The mixture was composed of 4 isomers in relative amounts of 14%, 36%, 23% and 25% (values established by gas chromatography). The configuration of the nitrites present in the mixture was attributed from the configuration of the starting cyclopentanol.

EXAMPLE 2

Preparation of the Aldehydes of the Invention

A. Preparation of (1R,2S,3R)-3-(2-Formyl-1-methylethyl)-1,2dimethyl-1-cyclopentyl Acetate Acetyl chloride (27 g; 0.34 mol) was added dropwise to a stirred solution of (1R,2S,3S)-3-isopropenyl-1,2-dimethyl-1-cyclopentanol (50 g; 0.32 mol), acetic anhydride (20 g; 0.2 mol), pyridine (57 g; 0.72 mol) and toluene (600 ml) at room temperature and heated to 45° C. during 3 days. The cooled reaction mixture was poured onto ice and washed with $H_2SO_4$ (10%), water, $NaHCO_3$ solution (5%) and brine, then distilled at 53–56°/0.7 hPa to give 59 g of (1R,2S,3S)-3-isopropenyl-1,2-dimethyl-1-cyclopentyl acetate of 90% purity. Fractional distillation finished 93% pure (1R,2S,3S)-3-isopropenyl-1,2-dimethyl-1-cyclopentyl acetate (48.7 g; 76.6%). This product showed an odor of the lactonic type, with connotations of jasmine and terpenyl acetate.

The compound was then subjected to a hydroformylation reaction under the conditions described in Example 1, to obtain the title compound.

B. Pyrolysis of (1R,2S,3R)-3-(2-Formyl-1-methylethyl)-1,2-dimethyl-1-cyclopentyl Acetate The thermolysis oven used was equipped with a quartz tube (length 1.8 m, diameter 30mm, filled with quartz granules over 30 cm), a dropping funnel and an outlet cooled with $CO_2$-acetone. At 25 hPa and 460° C., 34 g of the product obtained in A. was introduced dropwise. The thermolysate was distilled (45° C./0.6 hPa) to provide the aldehydes of formula (I") (20.9 g; 83.7%) as a mixture of isomers cis-(1'R)-3-(2'-methyl-3'-methylene-1'-cyclopentyl) butanal (36%), cis-(1'R)-(2',3'-dimethyl-2'-cyclopenten-1'-yl)butanal and cis-(1'R)-(2',3'-dimethyl-3'-cyclopenten-1'-yl)butanal.

The isomers can be separated by gas chromatography.

$^1$H-NMR: 0.83–1.02 (8d, 6H); 1.7 (br. s); 4.78 and 4.83 (2 spl. s); 5.23 and 5.27 (2, br. s); 9.8 (m, 1H) δ ppm (mixture); MS: 166($M^+$,6): 151(4), 148(2), 133(9), 122(77), 107(95), 95(100), 79(37), 67(52), 41(39) (not attributed); MS: 166 ($M^+$,4): 151(8), 148(10), 133(17), 122(22), 107(59), 95(100), 79(35), 67(43), 41(31) (not attributed); MS: 166 ($M^+$,13): 151(4), 148(3), 133(9), 122(76), 107(70), 95(100), 79(50), 67(62), 41(67) (not attributed); MS: 166($M^+$,2): 151(3), 148(4), 133(9), 122(41), 107(40), 95(100), 67(49), 41(47) (not attributed)

C. Preparation of (1'R,2'R)-3-(2',3'dimethyl-1'cyclopentyl) butanal

The hydrogenation of the product obtained in B. above (19.5 g) in ethyl acetate with 10% of a palladium/carbon catalyst finished the above-identified product (bp 50° C./0.5 hPa), 14.8 g (75%) as a mixture of 4 isomers in the relative amounts of 42%, 13%, 24% and 21%.

$^1$H-NMR: 0.63 and 0.66 (2d, J=7 Hz); 0.85–1.0 (d); 9.78 (m, 1H) δ ppm (mixture) MS: 168($M^+$,1): 153(3), 124(28), 109(59), 95(100), 81(19), 69(31), 55(68), 41(51) (not attributed); MS: 168($M^+$,0): 153(1), 124(33), 109(56), 95(92), 81(22), 69(43), 55(100), 41(68) (not attributed); MS: 168($M^+$,0): 124(30), 109(61), 95(100), 81(25), 69(30), 55(81), 41(59) (not attributed); MS: 168($M^+$,0): 153(1), 124(21), 109(48), 95(100), 81(13), 69(23), 55(65), 41(34) (not attributed).

EXAMPLE 3

Preparation of (1'R2'R)-3-(2',3'-dimethyl-1-cyclopentyl)butanenitrile

A mixture of the product obtained in Example 2C. (13.6 g=81 mmol), $NH_2OH.HCl$ (7.3 g; 105 mmol) and THF (150 ml) was refluxed during 3 h, then cooled and poured onto an ice/$NaHCO_3$ solution. Pentane was added and the organic phase washed, then distilled at ca 70° C./0.5 hPa to give 9.7 g (65.5%) of the corresponding oxime already containing some nitrile. This mixture was then refluxed with acetic anhydride (40 ml) during 4 h. After the usual treatment, the product was distilled at ca 50° C./6.6 hPa to give 7 g (81%) of the desired product as a mixture of 4 isomers in the relative amounts of 36%, 23%, 11% and 20%.

The isomers can be separated by gas chromatographic methods.

$^1$H-NMR: 0.62 and 0.63 (2d, J=7 Hz); 0.921.13 (8d) δ ppm (mixture); MS: 165($M^+$,0.1): 164(1), 150(14), 123(12), 110(69), 97(43), 70(71), 55(100), 41(66) (not attributed); MS: 165($M^+$,0.1): 164(1), 150(20), 123(10), 110(19), 97(36), 70(100), 55(94), 41(58) (not attributed); MS: 165 ($M^+$,0.1): 164(2), 150(28), 136(16), 122(19), 97(39), 70(81), 55(100), 41(62) (not attributed); MS: 165($M^+$,0.1): 164(1), 150(15), 122(14), 97(22), 70(100), 55(79), 41(48) (not attributed); MS: 165($M^+$,0.1): 164(1), 150(8), 136(4), 122 (5), 110(9), 97(12), 70(100), 55(56), 41(41), (not attributed); MS: 165($M^+$,0.1): 164(1), 150(7), 122(6), 97(13), 70(100), 55(52), 41(39) (not attributed).

EXAMPLE 4

Preparation of a Perfume for an All-purpose Cleaner

A perfuming base of the citrus type character, for use in an all-purpose cleaner, was prepared by admixing the following ingredients:

| Ingredients | Parts by weight |
| --- | --- |
| Hexyl acetate | 40 |
| 50% * C8-Aldehyde | 20 |
| 10% * C9-Aldehyde | 40 |
| 50% * C10-Aldehyde | 70 |
| Camphor | 25 |
| Citronellol | 80 |
| Dimyrcetol ® [1] | 150 |
| Hedione ® [2] | 50 |
| Geraniol | 45 |
| Geranyl nitrile [3] | 250 |
| Linalol | 120 |
| Orange terpenes | 570 |
| Terpineol | 140 |
| Terpinolene | 50 |
| Total | 1650 |

* in dipropyleneglycol
[1] mixture of 2,6-dimethyl-7-octen-2-ol and 1,1,5-trimethyl-6-heptenyl formate; origin: International Flavors & Fragrances, USA
[2] methyl dihydrojasmonate; origin: Firmenich SA, Geneva, Switzerland
[3] 3,7-dimethyl-2,6-octadienenitrile; origin: Firmenich SA, Geneva, Switzerland When there were added to this base composition 150 parts by weight of a nitrite according to the invention, for example of a mixture of compounds (I'a) of configuration (1'R,2'S, 3S) and (1'R,2'S,3R) and (I'b) of configuration (1'R,2'S,3R) and (1'R,2'S,3S), obtained according to the process described in Example 1, there was conferred to it a much fresher note. The green-natural, lemon-peel connotation present in the odor of the base composition due to the presence of geranyl nitrile was considerably enhanced. The addition of the compounds of the invention had the same effect as the addition of the same amount of citral, and the instability problem of the latter in a medium of the all-purpose cleaner type (see examples below) for which the described composition was intended, was thus obviated.

EXAMPLE 5

Preparation of a Perfume for a Powder Detergent

A composition of the floral-orange blossom type typical for a detergent formulation, was prepared from the following ingredients:

| Ingredients | Parts by weight |
| --- | --- |
| Linalyl acetate | 100 |
| Styrallyl acetate | 20 |
| Terpenyl acetate | 120 |
| Hexylcinnamic aldehyde | 140 |
| 10% * 2-Methyl-undecanal | 160 |
| Methyl anthranilate | 30 |
| Citronellol | 210 |
| Dihydromyrcenol | 650 |
| Diphenyloxyde | 10 |
| Lorysia ® [1] | 600 |
| Habanolide ® [2] | 270 |
| Helional [3] | 40 |
| Iralia ® [4] | 50 |
| Lavandin essential oil | 30 |
| Lilial ® [5] | 100 |
| Linalol | 140 |
| 10% * Crystal moss | 80 |
| 10% * 1,3-Dimethyl-3-phenylbutyl acetate [6] | 30 |
| Nerol | 70 |
| Polysantol ® [7] | 20 |
| Orange essential oil | 80 |
| 1-Methyl-4-(4-methyl-3-pentenyl)-3-cyclohexene carbaldehyde [8] | 40 |
| Amyl salicylate | 80 |
| 4-tert-Butyl-1-cyclohexanol [9] | 30 |
| α-Terpineol | 90 |
| Triplal ® [10] | 10 |
| Vertofix coeur [11] | 100 |
| Total | 3300 |

* in dipropyleneglycol
[1] 4-(1,1-dimethylethyl-1-cyclohexyl) acetate; origin: Firmenich SA, Geneva, Switzerland
[2] pentadecenolide; origin: Firmenich SA, Geneva, Switzerland
[3] 3-(1,3-benzodioxol-5-yl)-2-methylpropanal; origin: Firmenich SA, Geneva, Switzerland
[4] methylionone; origin: Firmenich SA, Geneva, Switzerland
[5] 3-(4-tert-butylphenyl)-2-methylpropanal; origin: Givaudan-Roure SA, Vernier, Switzerland
[6] origin: Firmenich SA, Geneva, Switzerland
[7] 3,3-dimethyl-5-(2,2,3-trimethyl-3-cyclopenten-1-yl)-4-penten-2-ol; origin: Firmenich SA, Geneva, Switzerland
[8] origin: Firmenich SA, Geneva, Switzerland
[9] origin: Firmenich SA, Geneva, Switzerland
[10] 2,4-dimethyl-3-cyclohexen-1-carbaldehyde; origin: International Flavors & Fragrances, USA
[11] origin: International Flavors & Fragrances, USA This composition acquires a nice citrus-green note of the lemon-lime type, which confers a remarkable freshness to the composition, when 50 parts of the mixture of compounds (I'a) of configuration (1'R,2'S,3S) and (1'R,2'S,3R) and (I'b) of configuration (I'R,2'S,3R) and (1'R,2'S,3S), obtained according to the process described in the above Example 1, are added thereto. The addition of the same amount of geranyl nitrile also confers a citrus-lemon type note to this composition, the resulting odor being however much fattier and less fresh, more reminiscent of lemongrass than of green-lemon.

COMPARATIVE EXAMPLES 1 to 6

The products and articles mentioned below were perfumed by adding to the appropriate unperfumed bases the mixture of compounds (I'a), of configuration (I'R,2'S,3S) and (1'R,2'S,3R), and (I'b), of configuration (1'R,2'S,3R) and (1'R,2'S,3S), obtained according to the process described in Example 1, geranyl nitrile and citral in the concentrations indicated, and then stored for 30 days at the temperatures indicated. The articles and products were then evaluated on a blind test by a panel of expert perfumers for their odor quality and, in some cases, their color change. The value of the resulting olfactive quality is indicated in the table below by the letter A to E having the following significations:

A=odor unchanged
B=odor slightly modified
C=odor clearly changed
D=odor strongly changed, becomes unpleasant
E=odor totally modified, cannot be recognized The intensity of the odor is signified on a scale from 1 (lowest) to 10 (highest). The color change is indicated by the abbreviations having the following significations:

SCo=slightly colored
Co=colored

TABLE

| | | Concentration (% by weight) | Temperature 3° | 22° | 40° |
| --- | --- | --- | --- | --- | --- |
| 1 Powder detergent containing perborates | Mixture of unsaturated nitriles of the invention | 0.2 | A8 | A8 | A7 |
| | Citral (pure) | 0.2 | B7 | D7 | E7 |
| | Geranyl nitrile | 0.2 | A10 | A9 | A8 |
| 2 Concentrated powder detergent | Mixture of unsaturated nitriles of the invention | 0.2 | A7 | A7 | B5 |
| | Citral (pure) | 0.2 | C4 | D6 | E6 |
| | Geranyl nitrile | 0.2 | A9 | A8 | B6 |
| 3 Antiperspirant (roll-on) | Mixture of unsaturated nitriles of the invention | 0.5 | A10 | B10 | B8 |
| | Citral (pure) | 0.5 | B8 | C8 | E8 |
| | Geranyl nitrile | 0.5 | A10 | A8 | B7 |
| 4 Antiperspirant (deo-stick) | Mixture of unsaturated nitriles of the invention | 0.5 | A10 | A10 | A9 |
| | Citral (pure) | 0.5 | C8 | D8 | E10 |
| | Geranyl nitrile | 0.5 | A10 | A8 | C6 |
| 5 Antiperspirant (dry-spray) | Mixture of unsaturated nitriles of the invention | 0.8 | A10 | A8 | A7 |
| | Citral (pure) | 0.8 | B10 | C9 | D9 |
| | Geranyl nitrile | 0.8 | B10 | B8 | B6 |
| 6 Soap | Mixture of unsaturated nitriles of the invention | 1 | A10 | A10 | A9 |
| | Citral (pure) | 1 | A7 | B7/Co | C7/Co |
| | Geranyl nitrile | 1 | A9 | B8 | B7/SCo |

These examples show that the product of the invention is even more stable than geranyl nitrile, known for its stability in aggressive media. It was furthermore demonstrated that the stability difference relative to citral, which is a product of a very prized odor in this type of application and to which the odor of the product of the present invention is very close, is quite pronounced, with the product of the invention being by far superior to citral stability-wise.

What is claimed is:
1. A method to improve, enhance. or modify the odor of a perfuming composition or a perfumed article comprising adding to said composition or said article an effective amount of a compound or a mixture of compounds of formula

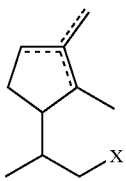 (I)

in which X is a C≡N group or a C(H)=O group and the C₅-ring is either saturated or carries a double bond in one of the positions indicated by the dotted lines.

2. A perfuming composition or perfumed article containing as a perfuming ingredient a compound, or a mixture of compounds, of formula

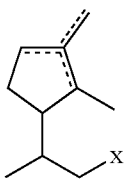 (I)

in which X is a C≡N group or a C(H)=O group and the C₅-ring is either saturated or carries a double bond in one of the positions indicated by the dotted lines.

3. Perfumed article according to claim 2, in the form of a perfume or cologne, a soap, a bath or shower gel, a shampoo or other hair care product, a cosmetic preparation, a body deodorant or antiperspirant, an air freshener, a fabric detergent or softener or an all-purpose household cleaner.

4. A body deodorant or antiperspirant, containing as a perfuming ingredient a compound, or a mixture of compounds of formula

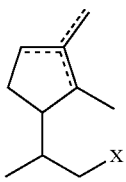 (I)

in which X is a C≡N group or a C(H)=O group and the C₅-ring is either saturated or carries a double bond in one of the positions indicated by the dotted lines.

5. A detergent containing as a perfuming ingredient a compound, or a mixture of compounds of formula

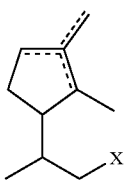 (I)

in which X is a C≡N group or a C(H)=O group and the C₅-ring is either saturated or carries a double bond in one of the positions indicated by the dotted lines.

6. The method of claim 1, wherein the compound or mixture of compounds is present in admixture with other perfuming ingredients, solvents, or adjuvants of current use in the art.

7. The method of claim 1, wherein X is C≡N.

8. The method of claim 7, wherein the compound or mixture of compounds comprises an isomer of formula

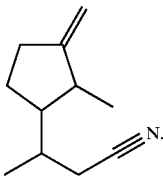 (Ia)

9. The method of claim 8, wherein the isomer of formula (Ia) is present in an amount of at least 30 percent by weight.

10. The method of claim 9, wherein the isomer of formula (Ia) has a configuration selected from the group consisting of (1'R, 2'S, 3S), (1'R, 2'S, 3R), and mixtures thereof.

11. A composition comprising a compound of formula

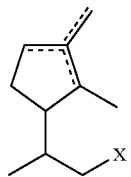 (I)

in which X is a C≡N group or a C(H)=O group and the C₅-ring is either saturated or carries a double bond in one of the positions indicated by the dotted lines, together with other perfuming ingredients, solvents, or adjuvants of current use in the art of perfumery.

12. The composition of claim 11, wherein X is C≡N.

13. The composition of claim 11, wherein the compound comprises an isomer of formula

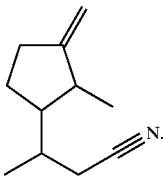 (Ia)

14. The composition of claim 13, wherein the isomer of formula (Ia) is present in an amount of at least 30 percent by weight.

15. The composition of claim 14, wherein the isomer of formula (Ia) has a configuration selected from the group consisting of (1'R, 2'S, 3S), (1'R, 2'S, 3R), and mixtures thereof.

16. The composition of claim 14, further comprising at least 60 percent by weight of an isomer of formula

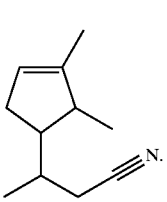 (Ib)

17. The composition of claim 16, wherein the isomer of formula (Ia) has a configuration selected from the group consisting of (1'R, 2'S, 3R) and (1'R, 2'S, 3S).

18. The perfuming composition of claim 2, wherein the compound or mixture of compounds is present in admixture with other perfuming ingredients, solvents, or adjuvants of current use in the art.

19. The perfuming composition of claim 2, wherein X is C≡N.

20. The perfuming composition of claim 2, wherein X is C(H)═O.

21. The body deodorant or antiperspirant of claim 4, wherein the compound or mixture of compounds is present in admixture with other perfuming ingredients, solvents, or adjuvants of current use in the art.

22. The body deodorant or antiperspirant of claim 4, wherein X is C≡N.

23. The body deodorant or antiperspirant of claim 4, wherein X is C(H)═O.

24. The detergent of claim 5, wherein the compound or mixture of compounds is present in admixture with other perfuming ingredients, solvents, or adjuvants of current use in the art.

25. The detergent of claim 5, wherein X is C≡N.

26. The detergent of claim 5, wherein X is C(H)═O.

27. The method of claim 9, wherein the mixture of compounds further comprises at least 60 percent by weight of an isomer of formula

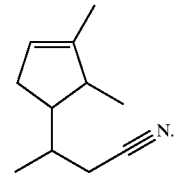

(Ib)

28. The method of claim 27, wherein the isomer of formula (Ia) has a configuration selected from the group consisting of (1'R, 2'S, 3R) and (1'R, 2'S, 3S).

\* \* \* \* \*

UNITED STATES PATENT AND TRADEMARK OFFICE
CERTIFICATE OF CORRECTION

PATENT NO. : 6,410,504 B1
DATED : June 25, 2002
INVENTOR(S) : Giersch

It is certified that error appears in the above-identified patent and that said Letters Patent is hereby corrected as shown below:

Column 1,
Line 45, change "nitrites" to -- nitriles --.

Column 2,
Lines 6, 9 (2 occurrences) and 46, change "nitrites" to -- nitriles --.

Column 3,
Lines 25 and 33, change "nitrites" to -- nitriles --.

Column 4,
Lines 9, 20, 39 and 57, change "nitrites" to -- nitriles --.

Column 5,
Lines 3, 10, 15, 16 and 17, change "nitrites" to -- nitriles --.

Column 6,
Lines 16, 23 and 49, change "nitrites" to -- nitriles --.

Column 7,
Line 9, change "Nitrites" to -- Nitriles --.

Column 8,
Line 65, change "nitrites" to -- nitriles --.

Column 10,
Lines 57 and 64, change "nitrite" to -- nitrile --.

Signed and Sealed this

Thirty-first Day of December, 2002

JAMES E. ROGAN
*Director of the United States Patent and Trademark Office*